(12) United States Patent
Goeke et al.

(10) Patent No.: US 10,450,532 B2
(45) Date of Patent: Oct. 22, 2019

(54) ORGANIC COMPOUNDS AND THEIR USE AS FRAGRANCE INGREDIENTS

(71) Applicant: GIVAUDAN SA, Vernier (CH)

(72) Inventors: Andreas Goeke, Winterthur (CH); Felix Flachsmann, Duebendorf (CH); Martin Alan Lovchik, Duebendorf (CH)

(73) Assignee: GIVAUDAN S.A., Vernier (CH)

( * ) Notice: Subject to any disclaimer, the term of this patent is extended or adjusted under 35 U.S.C. 154(b) by 0 days.

(21) Appl. No.: 15/528,242

(22) PCT Filed: Dec. 8, 2015

(86) PCT No.: PCT/EP2015/079009
§ 371 (c)(1),
(2) Date: May 19, 2017

(87) PCT Pub. No.: WO2016/091895
PCT Pub. Date: Jun. 16, 2016

(65) Prior Publication Data
US 2017/0327769 A1  Nov. 16, 2017

(30) Foreign Application Priority Data
Dec. 9, 2014  (GB) .................................. 1421855.6

(51) Int. Cl.
A61Q 13/00 (2006.01)
A61K 8/00 (2006.01)
C11B 9/00 (2006.01)
C07C 47/263 (2006.01)
C07C 33/046 (2006.01)

(52) U.S. Cl.
CPC .......... *C11B 9/0015* (2013.01); *C07C 33/046* (2013.01); *C07C 47/263* (2013.01)

(58) Field of Classification Search
CPC .... C11B 9/0015; C07C 47/263; C07C 33/046
USPC ................................ 512/27, 17, 16, 14, 8, 1
See application file for complete search history.

(56) References Cited

U.S. PATENT DOCUMENTS

| | | | |
|---|---|---|---|
| 3,381,039 A | 4/1968 | Marbet | |
| 3,953,518 A | 4/1976 | Wehrli | |
| 4,057,515 A | 11/1977 | Boelens et al. | |
| 5,969,190 A * | 10/1999 | Bauer .................. | C07F 7/1804 568/400 |
| 6,017,907 A * | 1/2000 | Bouillon ................ | C07C 35/22 514/167 |
| 9,469,590 B2 * | 10/2016 | Alchenberger .......... | C11D 3/50 |
| 2011/0305659 A1* | 12/2011 | Woo .......................... | A61L 9/01 424/76.21 |
| 2017/0247314 A1* | 8/2017 | Foley .................... | C07C 33/025 |

FOREIGN PATENT DOCUMENTS

| | | |
|---|---|---|
| GB | 981702 | 1/1965 |
| GB | 981702 A2 | 1/1965 |
| JP | 5291815 A | 8/1977 |
| WO | 9519963 A1 | 7/1995 |
| WO | 9852894 A1 | 11/1998 |
| WO | 2008087609 A2 | 7/2008 |
| WO | 2014198709 A1 | 12/2014 |
| WO | 2015181257 A2 | 12/2015 |

OTHER PUBLICATIONS

Plonska-Ocypa et al, Synthesis and biological evaluation of des-C,D-analog of 2-methylene-19-nor-1 alpha,25-(OH)2D3, 2007, Journal of Steroid and Biochemistry and Molecular Biology, 103, 298-304 (Year: 2007).*
International Search Report and Written Opinion of the International Searching Authority for corresponding application PCT/EP2015/079009 dated Feb. 3, 2016.
GB Search Report for corresponding application GB1421855.6 dated Sep. 15, 2015.
Bestmann, et al., "New Synthesis of Macrocyclic lactones", Angewandte Chemie, vol. 95, pp. 810-811, 1983.
Bestmann, et al., Synthesis, vol. 6, pp. 419-423, 1989.
Kutner, et al., "Synthesis of Retiferol RAD1 and RAD2, the Lead Representitives of a New Class of des-CD Analogs od Cholecalciferol1", Bioorganic Chemistry, vol. 23(1), 1995, pp. 22-32.
Plonska-Ocypa, et al., "Synthesis and biological evaluation of a des-C, D-analog of 2 methylene-19-nor-1alpha,25-(OH)2D3", Journal of Steroid Biochemistry and Molecular Biology, Elsevier Science Ltd., vol. 103, No. 3-5, pp. 298-304, Oxford, GB, Mar. 2007.
GB Search Report for GB 1313641.1 dated Jan. 29, 2014.
Anonymous, "Opinion of the Scientific Committee on Cosmetic Products and Non-Food Products Intended for Consumers Concerning Hydroxyisohexyl 3-Cyclohexene Carboxaldehyde", Dec. 2003, XP002726813, retrieved from the Internet, URL: http://ec.europa.eu/health/archive/ph_risk/committees/sccp/documents/out249_en.pdf.
International Search Report for corresponding application PCT/EP2014/062002 dated Aug. 4, 2014.
Written Opinion of the international Searching Authority for PCT/EP2014/062002 dated Aug. 4, 2014.
M.G. Vinogradov, et al., "Catalytic a-Alkylation of Aldehydes", Russian Bull. Chem.,1982, pp. 1265-1271.

* cited by examiner

*Primary Examiner* — Jessica Whiteley
(74) *Attorney, Agent, or Firm* — Norris McLaughlin PA

(57) ABSTRACT

A compound represented by the formula I

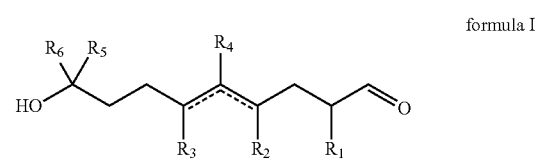

formula I wherein
⁓ is indicating a double bond either at C4 or at C5, or single bonds,
$R_1, R_2, R_3, R_4$ are independently selected from H or Me, and $R_5, R_6$ are independently selected from Me or Et,
and wherein the compound is not 9-hydroxy-5,9-dimethyl-dec-4-enal or 9-hydroxy-5,9-dimethyldecanal.
Said compounds are useful as perfume ingredients in personal care and household care products.

20 Claims, No Drawings

ORGANIC COMPOUNDS AND THEIR USE AS FRAGRANCE INGREDIENTS

This is an application filed under 35 USC 371 of PCT/EP2015/079009, filed 8 Dec. 2015, which in turn was based on GB 1421855.6 filed 9 Dec. 2014. This application claims the full priority benefit to the foregoing applications and also incorporates them here by reference as if set forth herein.

This invention relates to novel compounds, a method of preparing the compounds, and their use as fragrance ingredients, in particular its use as a fragrance ingredient to impart a muguet (lily of the valley) odour characteristic to a perfume composition. Still more particularly, the invention relates to said perfume preparations that contain no, or substantially no, Lyral™. The invention further relates to methods of making said perfume ingredients and perfume preparations, as well as the use of said perfume ingredients and perfume preparations in fine fragrances and consumer products, such as personal care and household care products. The invention also relates to perfume compositions and to articles, such as fine fragrances or consumer product compositions perfumed by the compound, or the perfume compositions containing said compound.

Compounds having muguet (or lily of the valley) odour characteristics are very sought after perfume ingredients. These compounds are important ingredients in floral bases and can act as harmonizers across many different types of fragrance creations. Compounds of this type are used widely in consumer products, such as personal care and consumer care products, as well as in fine perfumery, to generate pleasant odours or to mask unpleasant odours.

An excellent perfume ingredient widely valued for its muguet odour note is 4(4-hydroxy-4-methylpentyl) 3-cyclohexene carboxaldehyde, otherwise known as cyclohexal (Lyral™). This compound has found wide use in fine perfumery as well as in personal and household care products. However according to findings of the European Scientific Committee for Consumer Safety (SCCS) it has allergenic concerns and at the present time may be subject to regulatory action in the EU.

The problem addressed by the present invention is to provide new ingredients and new perfume preparations, in particular, which are perceived and recognised by perfumers as having substantially the same odour characteristics as cyclohexal, as well as having similar or even improved perfume performance compared to cyclohexal.

The applicant has now found compounds that can be employed as perfume ingredients in perfume compositions and consumer products. More particularly, the applicant has found compounds that possess desirable muguet odour characteristics. Still more particularly, the applicant has found compounds that possess odour characteristics, which may be perceived and recognised by perfumers as being very reminiscent of the odour of Lyral™ and so can serve as a simple replacement for Lyral™. Furthermore, the compounds may have similar or even improved perfume performance compared with Lyral™.

Accordingly, in a first aspect, the invention provides compounds represented by formula I

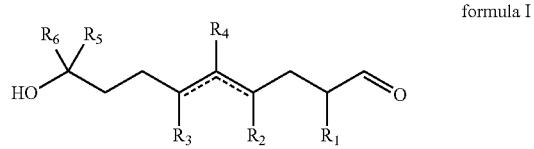

formula I

⌇ is indicating a double bond either at C4 or at C5, or single bonds,
$R_1$, $R_2$, $R_3$, $R_4$ are independently selected from H or Me, and
$R_5$, $R_6$ are independently selected from Me or Et,
and wherein the compound is not 9-hydroxy-5,9-dimethyldec-4-enal or 9-hydroxy-5,9-dimethyldecanal.

If a double bond is present in a compound of formula I, the configuration of the double bond is either E or Z, or the compound is a mixture E- and Z-isomers. The E- and Z-isomers may have different or similar individual odours. They may be used either in pure or enriched isomeric form or as isomeric mixture.

The compounds of the present invention possess individual odour characteristics. Some of the compounds of the present invention possess substantially similar odour characteristics and performance characteristics as Lyral™. As such, the present invention can achieve Lyral™ replacement based on a single compound. Such a replacement by a single fragrance might be cost-effective and convenient for a perfumer.

Furthermore, compounds of the present invention can generate particularly substantive and long-lasting muguet odour characteristics. Some of the compounds of the present invention might be particularly impactful perfume ingredients. As such, compounds of the present invention provide perfumers with an eminently suitable surrogate for the valuable yet problematic Lyral™.

Preferably, the compound of the invention is a compound represented by formula I as described above wherein $R_5$ and $R_6$ are two Me groups or one Me group and one Et group.

Preferably, the compound of the invention is a compound represented by formula I as described above wherein $R_1$ is H.

Preferably, the compound of the invention is a compound represented by formula I as described above wherein the total number of carbon atoms is not more than 15, even more preferred not more than 14.

In one aspect of the invention, there is provided a compound represented by formula I, wherein
⌇ is indicating a double bond either at C4 or at C5, or single bonds,
$R_1$, $R_2$, $R_3$, are independently selected from H or Me,
$R_4$ is H, and
$R_5$, $R_6$ are independently selected from Me or Et.

In another aspect of the invention, there is provided a compound represented by formula I, wherein
⌇ is indicating a double bond either at C4 or at C5, and the double bond is preferably located at C4, or single bonds,
$R_2$, $R_3$, are independently selected from H or Me,
$R_1$ and $R_4$ are H, and
$R_5$, $R_6$ are independently selected from Me or Et.

Preferably, the compound of formula I is selected from the group consisting of: 9-hydroxy-4,6,9-trimethyldec-4-enal, 9-hydroxy-6,9-dimethyldec-4-enal, 9-hydroxy-9-methyldec-4-enal, 9-hydroxy-4,6,9-trimethyldecanal, 9-hydroxy-6,9-dimethyldecanal, 9-hydroxy-9-methyldecanal, 9-hydroxy-5,9-dimethylundec-4-enal, 9-hydroxy-9-methylundecanal, 9-hydroxy-9-methyldec-5-enal and 9-hydroxy-2,5,9-trimethyldec-4-enal.

Accordingly, the invention provides in another of its aspects the use of a compound defined hereinabove as a perfume ingredient.

In particular, the invention provides in another of its aspects the use of a compound defined hereinabove in a perfume composition as a replacement for Lyral™.

In another aspect of the invention there is provided a method of imparting a muguet odour characteristic to a perfume composition, said method comprising the step of incorporating a compound defined hereinabove into said perfume composition.

In yet another aspect of the invention there is provided a perfume composition comprising a compound defined hereinabove.

In yet another aspect of the invention there is provided a perfume composition possessing muguet odour characteristics comprising a compound defined hereinabove.

In yet another aspect of the present invention there is provided a perfume composition comprising a compound defined hereinabove that is substantially free of Lyral™.

A perfume composition according to the present invention can be made up entirely by one or more of the compounds of the present invention. However, a perfume composition may also contain, in addition to one or more of the compounds of present invention, one or more additional perfume ingredients.

Compounds of the present invention may be present in a perfume composition in any amount depending on the particular olfactive effect that a perfumer wishes to achieve. In a particular embodiment of the present invention, a perfume composition of the present invention may contain compounds defined hereinabove in an amount of 0.1 to 100% by weight of said composition. In particular, the compounds may be employed in an amount of about 1 to 30%, more particularly 5-20%, by weight based on the total weight of said perfume composition If one or more additional perfume ingredients are employed, they may be selected from perfume ingredients known in the art.

Preferably, the at least one additional perfume ingredient that may be employed in a perfume composition possesses muguet odour characteristics, like (E/Z)-9-hydroxy-5,9-dimethyldec-4-enal.

The perfume composition may further comprise additional perfume ingredients. If one or more additional perfume ingredients are employed, they may be selected from any known perfume ingredients or from their precursor systems, respectively.

In particular, said perfume ingredients that may be employed in a perfume composition according to the invention include 3-(4-isobutyl-2-methylphenyl)propanal; 2-cyclohexylidene-2-phenylacetonitrile, e.g. PEONILE™; 4-(octahydro-4,7-methano-5H-inden-5-ylidene)butanal, e.g. DUPICAL™; 4-methyl-2-(2-methylpropyl)tetrahydro-2H-pyran-4-ol, e.g. FLOROSA™; and methyl 2-(2-hexyl-3-oxocyclopentyl)acetate, e. g. HEDIONE™.

Furthermore, perfume ingredients that may be employed in a perfume composition according to the invention include:

Natural ingredients, such as those selected from Iris, Mimosa, Ylang, Bergamot, jasmine and rose;

Synthetic muguet fragrance ingredients such as Cyclamen aldehyde (103-95-7), Hydroxydcitronellal (107-75-5), Hydroxy Citronellal diethyl acetal (7779-94-4), Lilial (80-54-6), Cyclohexal (31906-04-4), Silvial (6658-48-6), Bourgeonal (18127-01-0), Florhydral (125109-85-5), and Cyclemax (7775-00-0);

Harmonic floral ingredients of the rose type such as ethyl phenyl alcohol (60-12-8), Dimethyl phenyl ethyl carbinol (103-05-9), Citronellol (106-22-9), Rhodinol (106-22-9), Acet. DMBC (151-05-3), Geraniol (106-24-1), Nerol (106-25-2), Nerolidol (7212-44-4), Mefrosol (55066-48-3), Peomosa (19819-98-8), citronellyl iso butyrate (97-89-2), and Majantol (103694-68-4);

Harmonic foral ingredients of the freesia type such as Linalool (78-70-6), Rossitol (215231-33-7), and Coranol (83926-73-2);

Harmonic floral ingredients of the lilac type such as Alc. Cinnamic alcohol (104-54-1), propyl phenyl alcohol (122-97-4) and Terpineol (8000-41-7);

Harmonic floral ingredients of the jasmine type such as benzyl acetate (140-11-4), Hedione (24851-98-7), Hexyl Cinnamic aldehyde (101-86-0), and Amyl Cinnamic aldehyde (122-40-7);

Harmonic floral ingredients of the muguet type such as Super Muguet (26330-65-4), Hydroxydtronellal dimethyl acetate (141-92-4), Magnol (92046-49-6), Mugetanol (63767-86-2), Mugesia (56836-93-2), Indole (120-72-9), and Indolene (67860-00-8);

Green harmonic ingredients such as ds 3 Hexenol (928-96-1), phenyl acetic aldehyde (122-78-1), Maceal (67845-30-1), ds 3 hexenyl acetate (3681-71-8), Acetal CD (29895-73-6), Precarone (74499-58-4), Mefranal (55066-49-4), Elintaal (40910-49-4), Glycolierral (68901-32-6), and Coranol (83926-73-2); Fresh harmonic ingredients such as C11 undecelenic aldehyde (112-45-8), C11 undecylic aldehyde (112-44-7), C 10 aldehyde (112-31-2), C 12 MNA aldehyde (110-41-8), Tropional (1205-17-0), Citral (5392-40-5), Oxyde de Limette (73018-51-6), Florhydral (125109-85-5), Floralozone (67634-15-5), Dihydro Farnesal (51513-58-7), Dihydrofarnesol (51411-24-6), Adoxal (141-13-9), Citronellyl Oxyacetaldehyde (7492-67-3), Floral super (71077-31-1) and Dodecenal (4826-62-4);

Harmonic woody ingredients such as Irisone (8013-90-9) and methyl Ionone (1335-46-2);

Harmonic powdery ingredients such as Fixolide (21145-77-7), Thibetolide (106-02-5), Héliotropine (120-57-0) and Vanilline (121-33-5); and Diverse harmonic floral ingredients such as Phixia (107-75-5), Farnesal (19317-11-4), Farnesyle acetate (29548-30-9), Rhodinyl acetate (141-11-7), Cyclomethylene Citronellol (15760-18-6), Mayol (5502-75-0), Myraldyl acetate (72403-67-9), and Melonia (3613-30-7), wherein the CAS numbers of the molecules are provided in parentheses.

In addition to the aforementioned perfume ingredients that may be employed as being particularly complimentary to the odour characteristics of the compound of formula (I), other fragrance ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odourants obtained from natural products and the like. However, it is preferred that the perfume compositions contain no, or substantially no, cyclohexal.

The perfume ingredients contained in said perfume composition are described above, but of course, the perfume composition may not be limited to the stated ingredients. In particular, perfume mixtures may comprise adjuvants that are commonly employed in perfume formulations. The term "adjuvants" refers to an ingredient that might be employed in a perfume composition for reasons other than, or not specifically, related to the composition's olfactive performance. For example, an adjuvant may be an ingredient that acts as an aid to processing a perfume ingredient or ingredients, or a composition containing said ingredient(s), or it may improve handling or storage of a perfume ingredient or composition containing same. It might also be an ingredient that provides additional benefits such as imparting colour or texture. It might also be an ingredient that imparts light resistance or chemical stability to one or more ingredients contained in a perfume ingredient or composition containing same. A detailed description of the nature and type of adjuvants commonly used in perfume mixture or compositions containing same cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

In a particular embodiment of the present invention a composition comprising a compound of formula (I), or perfume composition containing same, as herein defined, contains an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9). More specifically, Tinogard Q in triethyl citrate (TEC) can be preferentially used as an antioxidant of the compound of formula (I). The antioxidants may be applied in levels of 0.5 to 3% in the neat compound of formula (I).

Applicant found that unless precautions are taken to prevent excessive oxidation of compound of formula (I), undesirable levels of oxidation products can be produced. When used in certain levels, the oxidation products can be employed to compliment the odour characteristic of the compound of formula (I). However, for reasons related to olfactive quality, the levels of oxidation products should not be too high. Accordingly, an anti-oxidant may be employed in combination with the compound of formula (I).

Furthermore, any one or more of the perfume ingredients or adjuvants employed in the present invention might be formulated in a delivery vehicle if desired to provide a desired effect. Delivery vehicles may include encapsulates. Alternatively, a delivery vehicle may be in the form of a solid support, e.g. a polymeric support material onto which one or more perfume ingredients or adjuvants may be chemically or physically bound. Still further, one or more perfume ingredients or adjuvants may be dissolved or dispersed in a matrix material, which serves to control the rate at which said ingredient or ingredients emanates therefrom. In yet an alternative embodiment, one or more ingredients or adjuvants may be supported on a porous substrate, such as a cyclodextrin or a zeolite or other inorganic material. In a still further embodiment, one or more perfume ingredients may be provided in the form of a pro-perfume, which will react in a suitable environment to release the perfume ingredient in a controlled manner.

Preferably, in case of further perfume ingredients bearing a carbonyl functionality, the corresponding pro-perfume is a reaction product of a primary and/or secondary amine compound and the perfume ingredient.

In particular it is preferred that such a pro-perfume, also known as fragrance precursor, is a reaction product of a suitable amino compound and a compound represented by the formula I

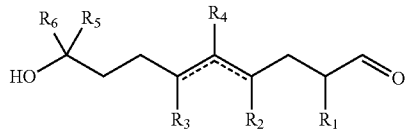

formula I wherein
⌒ is indicating a double bond either at C4 or at C5, or single bonds,
$R_1$, $R_2$, $R_3$, $R_4$ are independently selected from H or Me, and
$R_5$, $R_6$ are independently selected from Me or Et,
and wherein the compound is not 9-hydroxy-5,9-dimethyl-dec-4-enal or 9-hydroxy-5,9-dimethyldecanal.

Preferably, the pro-perfume is a reaction product of a suitable amino compound and a compound represented by formula I as described above wherein $R_5$ and $R_6$ are two Me groups or one Me group and one Et group.

Preferably, the pro-perfume is a reaction product of a suitable amino compound and a compound represented by formula I as described above wherein $R_1$ is H.

Preferably, the pro-perfume is a reaction product of a suitable amino compound and a compound represented by formula I as described above, wherein the total number of carbon atoms is not more than 15, even more preferred not more than 14.

In one aspect of the invention, it is preferred that the pro-perfume is a reaction product of a suitable amino compound and a compound represented by formula I, wherein
⌒ is indicating a double bond either at C4 or at C5, or single bonds,
$R_1$, $R_2$, $R_3$, are independently selected from H or Me,
$R_4$ is H, and
$R_5$, $R_6$ are independently selected from H, Me or Et.

In another aspect of the invention, it is preferred, that the pro-perfume is a reaction product of a suitable amino compound and a compound represented by formula I, wherein
⌒ is indicating a double bond either at C4 or at C5, and the double bond is preferably located at C4, or single bonds,
$R_2$, $R_3$, are independently selected from H or Me,
$R_1$ and $R_4$ are H, and
$R_5$, $R_6$ are independently selected from H, Me or Et.

It is particularly preferred that the pro-perfume is a reaction product of a suitable amino compound and a compound selected from the group consisting of: 9-hydroxy-4,6,9-trimethyldec-4-enal, 9-hydroxy-6,9-dimethyldec-4-enal, 9-hydroxy-9-methyldec-4-enal, 9-hydroxy-4,6,9-trimethyldecanal, 9-hydroxy-6,9-dimethyldecanal, 9-hydroxy-9-methyldecanal, 9-hydroxy-5,9-dimethylundec-4-enal, 9-hydroxy-9-methylundecanal, 9-hydroxy-9-methyldec-5-enal and 9-hydroxy-2,5,9-trimethyldec-4-enal.

By such a reaction, different products may be obtained, for example the corresponding imine, enamine, hemi-aminal or aminal.

A suitable amino compound for formation of the above mentioned pro-perfume can be selected from the group consisting of aromatic amines, in particular methyl 2-aminobenzoate (methyl anthranilate), 2-amino-acetophenone, ortho, meta or para aminobenzoates; primary or secondary aliphatic amines, preferably C8-C30 linear or branched alkylamines or alkyldiamines; etheramines; ethylene- and propylene-amines; amino adds and derivatives; polyamines, in particular primary and secondary polyetheramines, polyethyleneimines, polypropyleneimines, polyamidoamines, polyamino adds, polyvinylamines, poly(ethylene glycol) bis(amine), amino substituted polyvinylalcohols; N-(3-aminopropyl)imidazole, nipecotamide, skatole and indole.

Alternatively, the pro-perfume suitable to release a compound of formula I may be provided as a product of a Knoevenagel condensation, or an aldol condensation, as an oxidative cleavable pro-perfume or an acetal or hemi-acetal.

Having regard to the foregoing, it will be appreciated that a perfume composition may be at least partly in solid form, in gel form, in foam form and/or liquid form. If it is present in solid form, it then it may take the form of granules, powders or tablets.

The present invention provides in another of its aspects a fine fragrance or consumer product, such as a personal care or household care composition that is perfumed by a compound represented by the formula I

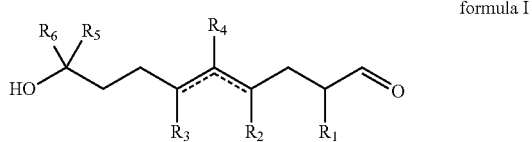

formula I wherein
⌢ is indicating a double bond either at C4 or at C5, or single bonds,
$R_1$, $R_2$, $R_3$, $R_4$ are independently selected from H or Me, and
$R_5$, $R_6$ are independently selected from Me or Et,
and wherein the compound is not 9-hydroxy-5,9-dimethyldec-4-enal or 9-hydroxy-5,9-dimethyldecanal.

Preferably, said fine fragrance or consumer product is perfumed by the compound represented by formula I as described above wherein $R_5$ and $R_6$ are two Me groups or one Me group and one Et group.

Preferably, said fine fragrance or consumer product is perfumed by the compound represented by formula I as described above wherein $R_1$ is H.

Preferably, said fine fragrance or consumer product is perfumed by the compound represented by formula I as described above wherein the total number of carbon atoms is not more than 15, even more preferred not more than 14.

Preferably, said fine fragrance or consumer product is perfumed by a compound represented by the formula I, wherein
⌢ is indicating a double bond either at C4 or at C5, or single bonds,
$R_1$, $R_2$, $R_3$, are independently selected from H or Me,
$R_4$ is H, and
$R_5$, $R_6$ are independently selected from Me or Et.

In another aspect of the invention, said fine fragrance or consumer product is perfumed by a compound represented by the formula I, wherein
⌢ is indicating a double bond either at C4 or at C5, and the double bond is preferably located at C4, or single bonds,
$R_2$, $R_3$, are independently selected from H or Me,
$R_1$ and $R_4$ are H, and
$R_5$, $R_6$ are independently selected from Me or Et.

In yet more particular embodiments of the present invention there is provided a fine fragrance or consumer product, such as a personal care or household care composition that is perfumed by at least one or more compounds selected from 9-hydroxy-4,6,9-trimethyldec-4-enal, 9-hydroxy-6,9-dimethyldec-4-enal, 9-hydroxy-9-methyldec-4-enal, 9-hydroxy-4,6,9-trimethyldecanal, 9-hydroxy-6,9-dimethyldecanal, 9-hydroxy-9-methyldecanal, 9-hydroxy-5,9-dimethylundec-4-enal, and 9-hydroxy-9-methylundecanal, 9-hydroxy-9-methyldec-5-enal and 9-hydroxy-2,5,9-trimethyldec-4-enal, or the corresponding pro-perfumes.

The compounds or pro-perfumes defined above, when added to a fine fragrance or consumer product, such as a personal care or household care composition, impart a characteristic muguet odour to said compositions. According to another aspect of the present invention there is provided a method of imparting muguet odour characteristics to a fine fragrance or consumer product, such as a personal care or household care composition comprising the step of adding to said composition a compound defined above or a perfume composition containing said compound.

In yet another aspect of the invention there is provided a method of imparting muguet odour characteristics to a fine fragrance or consumer product, such as a personal care or household care composition, comprising the step of selectively adding to said fine fragrance or consumer product a compound of formula (I) as defined above, and selectively excluding from said fine fragrance or consumer product Lyral™.

Consumer products, such as personal and household care compositions include, but are not limited to a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover and/or a precursor of the aforementioned products.

The skilled person is fully aware of the applicability of perfume ingredients, and compositions to fine fragrance applications, as well as all manner of consumer product applications, such as personal and house hold care compositions and a very detailed description of such compositions is not warranted here. However, specific compositions that can be mentioned include cleaning compositions; autocare compositions; Cosmetic compositions; textile treatment compositions; and air freshener and air care compositions.

Cleaning products include:—

Toilet cleaners or lavatory cleaners, in other words, products for cleaning lavatory bowls and urinals, these products being supplied preferably in the form of powders, blocks, tablets or liquids, preferably gels. Besides other typical ingredients such as surfactants, they generally include organic acids e.g., citric acid and/or lactic add) or sodium hydrogen sulfate, amidosulfuric add or phosphoric acid for removing limescale or urine scale;

Pipe-cleaning products or drain cleaners. These are typically strongly alkaline products which serve in general to remove pipe blockages comprising organic materials-such as hair, fat, food residues, soap deposits, and the like. Additions of Al powder or Zn powder may serve for the formation of H2 gas with an effervescence effect. Possible ingredients are commonly alkalis, alkaline salts, oxidizing agents, and neutral salts. Supply forms in powder form preferably also include sodium nitrate and sodium chloride. Pipe-cleaning products in liquid form may preferably also include hypochlorite. There are also enzyme-based drain cleaners as well. Acidic products are likewise possible;

Universal or all-purpose or general-purpose cleaners. These are cleaners which can be used universally for all hard surfaces in the household and in commerce that can be wiped down wet or damp. Generally speaking, they are neutral or slightly alkaline or slightly acidic products, especially liquid products. All-purpose or general-purpose cleaners generally contain surfactants, builders, solvents and hydrotropes, dyes, preservatives, and the like;

All-purpose cleaners with special disinfectant properties. They additionally include active antimicrobial ingredients (e.g., aldehydes, alcohols, quaternary ammonium compounds, amphoteric surfactants, triclosan);

Sanitary cleaners. These are products for cleaning in bath and toilet. The alkaline sanitary cleaners are used preferably for removing fatty soiling, whereas the acidic sanitary cleaners are employed in particular, for removing limescale. Sanitary cleaners advantageously also have a considerable disinfectant action, particularly the strongly alkaline sanitary cleaners that contain chlorine;

Oven cleaners or grill cleaners which may be supplied in the form of gels or foam sprays. They generally serve for removing burnt-on or carbonized food residues. Oven cleaners are preferably given a strongly alkaline formulation using, for example, sodium hydroxide, sodium metasilicate, 2-aminoethanol. In addition they generally contain anionic and/or nonionic surfactants, water-soluble solvents, and, in some cases, thickeners such as polycarboxylates and carboxymethylcellulose;

Metal polishes. These are cleaners for particular types of metal such as stainless steel or silver. Stainless steel cleaners preferably contain, besides adds (preferably up to 3% by weight, e.g., citric acid, lactic add), surfactants (in particular, up to 5% by weight, preferably nonionic and/or anionic surfactants), and water, solvents as well (preferably up to 15% by weight) to remove fatty soiling, and also further compounds such as thickeners and preservatives. Very fine polishing structures are included, furthermore, in products for preferably bright stainless steel surfaces. Silver polishes, in turn, may be provided in an acidic formulation. In particular, for removing black deposits of silver sulfide they contain, preferably, complexing agents (e.g., thiourea, sodium thiosulfate). Typical supply forms are polishing cloths, dipping baths, pastes, and liquids. Dark discolorations (oxide layers) are removed using copper cleaners and nonferrous-metal cleaners (e.g., for brass and bronze). They generally have a weakly alkaline formulation (preferably with ammonia) and in general contain polishing agents and also, preferably, ammonium soaps and/or complexing agents;

Glass cleaners and window cleaners. These products serve preferably to remove dirt, especially greasy dirt, from glass surfaces. Preferably they contain compounds such as anionic and/or nonionic surfactants (in particular, up to 5% by weight), ammonia and/or ethanolamine (in particular, up to 1% by weight), ethanol and/or 2-propanol, glycol ethers (in particular, 10-30% by weight), water, preservatives, dyes, anti-misting agents and the like;

Special-purpose cleaning products, examples being those for glass-ceramic hobs, and also carpet cleaners and stain removers.

Autocare products include:—
Paint preservers, paint polishes, paint cleaners, wash preservers, shampoos for auto washing, auto-wash and wax products, polishes for trim metals, protective films for trim metals, plastics cleaners, tar removers, screen cleaners, engine cleaners, and the like.

Cosmetic products include:—
(a) cosmetic skincare products, especially bath products, skin washing and cleansing products, skincare products, eye makeup, lip care products, nail care products, intimate care products, foot care products;
(b) cosmetic products with specific effects, especially sunscreens, tanning products, de-pigmenting products, deodorants, antiperspirants, hair removers, shaving products, perfumes;
(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

Textile treatment products include:—
Detergents or fabric conditioners, for example, in either liquid or solid form.

Air fresheners and room fragrancers include:—
Products that contain preferably volatile and usually pleasant-smelling compounds which advantageously can even in very small amounts mask unpleasant odours. Air fresheners for living areas contain, in particular, natural and synthetic essential oils such as pine needle oils, citrus oil, *eucalyptus* oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants. Other presentation forms include sticks and blocks. They are produced typically using a gel concentrate comprising essential oils. It is also possible to add formaldehyde (for preservation) and chlorophyll (preferably <5% by weight), and also further ingredients. Air fresheners are not, however, restricted to living spaces, but may also be intended for autos, cupboards, dishwashers, refrigerators or shoes, and even their use in vacuum cleaners is a possibility. In the household (e.g., in cupboards), for example, in addition to the odour improvers, disinfectants as well are employed, containing preferably compounds such as calcium phosphate, talc, stearin, and essential oils, these products taking the form, for example, of sachets.

There now follows a series of examples that serve to further illustrate the invention.

Example 1: Preparation of
9-hydroxy-4,6,9-trimethyldec-4-enal 1a) 2,4,7-Trimethylocta-1,6-dien-3-ol

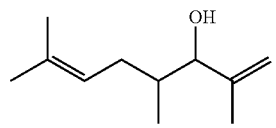

The solution of 2,5-dimethylhex-4-enal (10.0 g, 79 mmol) in THF (40 ml) was added to solution of prop-1-en-2-ylmagnesium bromide (0.5 N in THF, 190 ml, 95 mmol, 1.2 equiv.) at 5-10° C. (icebath) and the resulting mixture was stirred at room temperature for 20 h. Saturated aq. NH$_4$Cl solution was added dropwise until pH 4, then the mixture was partitioned between MTBE and water, the aqueous layer was extracted with MTBE and the combined organic layers washed with brine and dried over MgSO$_4$. The solvent was removed and the residual crude oil distilled at 46° C./0.06 mbar to yield a colourless liquid (7.4 g, 56%; 2 diastereomers, ratio 56:44).

$^1$H-NMR (CDCl$_3$, 400 MHz): 5.23-5.11 (m, 1H), 4.98-4.83 (m, 2H), 3.90 (t, J=4.6 Hz, 0.56H), 3.80 (dd, J=7.6, 4.4 Hz, 0.44H), 2.25 (s, 1H), 2.32-2.22 (m, 0.44H), 2.07 (td, J=14.4, 6.5 Hz, 0.56H), 1.96-1.80 (m, 1H), 1.73-1.70 (m, 6H), 1.69-1.66 (m, 1H), 1.63 (br. s, 1.3), 1.62 (br. s, 1.7H), 0.87 (d, J=6.6 Hz, 1.7H), 0.81 (d, J=6.8 Hz, 1.3H). $^{13}$C-NMR (CDCl$_3$, 100 MHz): 146.8 (s), 146.5 (s), 132.7 (s), 132.7 (s), 122.9 (d), 122.8 (d), 112.5 (t), 111.1 (t), 80.9 (d), 78.7 (d), 36.6 (d), 36.2 (d), 32.2 (t), 30.5 (t), 25.9 (q), 25.8 (q), 18.5 (q), 17.8 (q), 17.8 (q), 17.3 (q), 16.2 (q), 13.5 (q). MS (EI, 70 eV, main isomer): 168 (M$^+$, 2), 153 (2), 135 (5), 125 (6), 107 (21), 96 (24), 81 (21), 69 (35), 55 (100), 41 (50).

1b) 4,6,9-Trimethyldeca-4,8-dienal

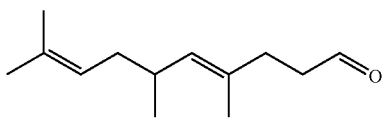

The mixture of 2,4,7-trimethylocta-1,6-dien-3-ol (6.0 g, 35.7 mmol), ethoxy ethene (28.3 g, 392 mmol, 11 equiv) and phenyl phosphonic add (20 mg) was heated in an autoclave to 180° C. (14 bar) during 1 h, then concentrated under vacuum and the residue was purified by two flash chromatographies, the first eluting with hexane/EtOAc 79:1, then hexane/EtOAc 39:1 to yield 4,6,9-trimethyldeca-4,8-dienal (2.1 g, 30%) as a colourless oil, and 3-(1-ethoxyethoxy)-2,4,7-trimethylocta-1,6-diene (yellow oil, 4.9 g, 57%, E/Z isomers, ratio ca. 4:1).

4,6,9-Trimethyldeca-4,8-dienal $^1$H-NMR (CDCl$_3$, 400 MHz): 9.77 (t, J=1.7 Hz, 0.2H), 974 (t, J=2.0 Hz, 0.8H), 5.13-5.02 (m, 1H), 5.01-4.94 (m, 1H), 2.54-2.45 (m, 2H), 2.40-2.27 (m, 3H), 2.00-1.84 (m, 2H), 1.69-1.66 (m, 3.5H), 1.61 (d, J=1.2 Hz, 2.5H), 1.58 (s, 3H), 0.91 (d, J=6.6 Hz, 0.6H), 0.90 (d, J=6.6 Hz, 2.4H). $^{13}$C-NMR (CDCl$_3$, 100 MHz): 202.7 (d), 202.3 (d), 133.2 (d), 132.1 (d), 132.1 (s), 131.9 (s), 131.3 (s), 131.1 (s), 122.9 (d), 42.6 (t), 42.1 (t), 35.9 (t), 35.8 (t), 33.0 (d), 32.9 (d), 31.9 (t), 25.8 (q), 24.5 (t), 23.1 (q), 20.9 (q), 20.5 (q), 17.8 (q), 16.2 (q). MS (EI, 70 eV, main isomer): 194 (M$^+$, <1), 178 (<1), 125 (100), 107 (52), 97 (16), 91 (18), 83 (27), 69 (32), 55 (96), 41 (56).

1c) 9-Hydroxy-4,6,9-trimethyldec-4-enal

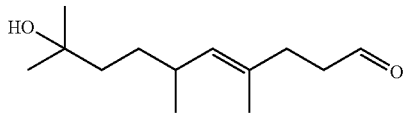

The solution of 4,6,9-trimethyldeca-4,8-dienal (0.50 g, 2.57 mmol) in CH$_2$Cl$_2$(7 ml) was cooled to 0° C., trifluoroacetic acid (1.47 g, 12.9 mmol, 5 equiv.) was added and the resulting mixture stirred at 0° C. for 80 min. Then concentrated aq. Na$_2$CO$_3$ solution was added until pH 8 was reached and the mixture was extracted with MTBE, the organic layer was washed with brine, dried over MgSO$_4$ and concentrated in vacuo. The residue was dissolved in methanol and sodium methoxide (139 mg, 2.57 mmol, 1 equiv.) was added. The mixture was stirred for 1 h at room temperature, then diluted with water and extracted with MTBE. The organic layer was washed with water, 10% aq. AcOH and brine, dried over MgSO$_4$ and concentrated in vacuo. The residue was purified by flash chromatography on SiO$_2$ eluting with hexane/EtOAc 14:1 to obtain 9-hydroxy-4,6,9-trimethyldec-4-enal (slightly yellow oil, 37 mg, 7%, E/Z isomers, ratio ca. 4:1).

$^1$H-NMR (CDCl$_3$, 400 MHz): 9.77 (t, 3=1.7 Hz, 0.2H), 9.73 (t, 3=2.0 Hz, 0.8H), 4.91 (qd, 3=1.2, 9.5 Hz, 1H), 2.57-2.43 (m, 2H), 2.40-2.21 (m, 3H), 1.67 (d, 3=1.2 Hz, 0.6H), 1.60 (d, 3=1.5 Hz, 2.4H), 1.41-1.32 (m, 4H), 1.30-1.15 (m, 1H), 1.18 (2× br. s, 6H), 0.92 (d, 3=6.9 Hz, 0.6H), 0.91 (d, 3=6.9 Hz, 2.4H). $^{13}$C-NMR (CDCl$_3$, 100 MHz): 202.7 (d), 202.2 (d), 133.3 (d), 132.2 (d), 131.6 (s), 131.5 (s), 70.8 (s), 42.1 (t), 41.7 (t), 41.6 (t), 32.7 (d), 32.2 (t), 32.1 (t), 31.9 (t), 29.2 (q), 29.2 (q), 24.5 (t), 23.0 (q), 21.6 (q), 21.2 (q), 16.3 (q). MS (EI, 70 eV, main isomer): 194 ([M-H$_2$O+], <1), 179 (1), 161 (8), 138 (28), 121 (13), 109 (75), 96 (100), 81 (32), 67 (22), 59 (65), 53 (61), 43 (65).

Odour description: lily of the valley, rosy, aldehydic.

Example 2: Preparation of 9-hydroxy-9-methyldec-4-enal

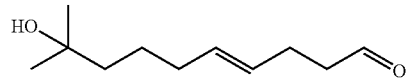

9-Methyldeca-4,8-dienal was prepared according to X. Wei, Xudong, J. C. Lorenz, S. A. Suresh, N. Haddad, C. A. Busacca, C. H. Senanayake, J. Org. Chem. 2007, 72(11), 4250-4253.

Formic acid (2.49 g, 54.1 mmol, 10 equiv.) was added at 0° C. to 9-methyldeca-4,8-dienal (0.9 g, 5.4 mmol) and the mixture was stirred at 0° C. for 6 h, then extracted with ethyl acetate. The organic layer was washed with water, sat. aq. NaHCO$_3$ solution and brine, dried over MgSO$_4$ and concentrated in vacuo. The residue was purified by flash chromatography on SiO$_2$ eluting with hexane/EtOAc/EtOH 15:4:1 to yield 9-hydroxy-9-methyldec-4-enal (slightly yellow oil, 101 mg, 10%, R$_f$=0.13, >99% E-isomer).

$^1$H-NMR (CDCl$_3$, 400 MHz): 9.76 (t, 3=1.6 Hz, 1H), 5.52-5.34 (m, 3H), 2.49 (td, 3=6.4, 0.8, 1H), 2.35 (q, 3=6.4, 1H), 2.05-1.95 (m, 2H), 1.46-1.32 (m, 4H), 1.28-1.17 (m, 2H), 1.21 (s, 6H). $^{13}$C-NMR (CDCl$_3$, 100 MHz): 202.4 (d), 131.7 (d), 128.1 (d), 70.9 (s), 43.5 (t), 43.3 (t), 32.9 (t), 29.2 (q), 25.2 (t), 24.1 (t). MS (EI, 70 eV, main isomer): 169 ([M–CH$_3$$^+$], <1), 151 (1), 133 (5), 122 (7), 110 (24), 82 (31), 67 (27), 59 (100), 55 (31), 43 (40).

Odour description: floral-green, lily of the valley, aldehydic.

Example 3: Preparation of 9-hydroxy-9-methyldecanal

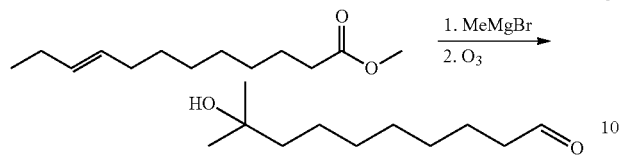

3a: 2-Methyltridec-10-en-2-ol

A solution of methyl-9-dodecanoate (20 g, 94 mmol) in THF (150 ml) was cooled to 0° C. and a solution of methyl magnesiumchloride (109.9 ml, 3M in THF) was added while keeping the temperature below 31° C. The mixture was stirred for 1.5 h and poured into a saturated solution of NH$_4$Cl (200 ml). The mixture was extracted twice with MTBE (200 ml) and the combined organic phases were washed with water (200 ml) and brine (200 ml), dried (MgSO$_4$) and evaporated in vacuo to yield crude 2-methyl-tridec-10-en-2-ol (19.33 g, 97%).

3b: 9-Hydroxy-9-methyldecanal

A solution of 2-methyltridec-10-en-2-ol (8.3 g, 39.1 mmol, crude) in a mixture of dichloromethane (60 ml) and methanol (60 ml) was cooled to −75° C. Ozone was bubbled though the solution until the color changed to slightly blue. A stream of oxygen was bubbled though the solution until the blue color disappeared. The reaction flask was twice evacuated and flushed with nitrogen to remove oxygen and palladium on charcoal (0.2 g) was added. The temperature was allowed to rise to −25° C., the nitrogen atmosphere was replaced with hydrogen and the mixture was hydrogenated while keeping the temperature at below 30° C. with help of an ice bath. The solution was filtered, evaporated in vacuo and the residue was purified by chromatography on silica gel (eluent:hexane:MTBE 1:1) to yield 9-hydroxy-9-methyl decanal (2.5 g, 33%) as a colorless oil.

$^1$H-NMR (CDCl$_3$, 400 MHz): 9.76 (t, J=1.9 Hz, 1H), 3.66 (bs, 1H), 2.42 (dt, J=1.9, 7.4 Hz, 2H), 1.66-1.58 (m, 2H), 1.47-1.43 (m, 2H), 1.38-1.26 (m, 8H), 1.20 (s, 6H) ppm. $^{13}$C-NMR (CDCl$_3$, 100 MHz): 202.9 (d), 71.1 (s), 43.8 (2t), 29.9 (t), 29.1 (2q), 29.1 (t), 24.2 (2t), 22.0 (t) ppm. MS (EI, 70 eV): 171 ([M−CH$_3$]$^+$6), 135 (2), 110 (3), 95 (9), 83 (5), 69 (7), 59 (100), 43 (23), 29 (8).

Odor description: fresh, floral, muguet.

Example 4: Preparation of 9-hydroxy-9-methylundecanal

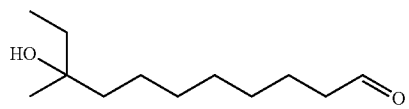

This compound was synthesized according to the proceeding described in Example 3, using 1 equivalent of methyl magnesium chloride and 1 equivalent of ethyl magnesium bromide.

$^1$H-NMR (CDCl$_3$, 400 MHz): 9.77 (t, J=1.7 Hz, 1H), 3.52 (bs, 1H), 2.43 (dt, J=1.7, 7.3 Hz, 2H), 1.67-1.60 (m, 2H), 1.48 (qm J=7.6 Hz, 2H), 1.45-1.41 (m, 2H), 1.37-1.26 (m, 8H), 1.14 (s, 3H) 0.89 (t, J=7.6 Hz, 3H) ppm. $^{13}$C-NMR (CDCl$_3$, 100 MHz): 202.9 (d), 72.9 (s), 43.9 (t), 41.3 (t), 34.2 (t), 30.0 (t), 29.3 (t), 29.1 (t), 26.4 (q), 23.8 (t), 22.1 (t), 8.2 (q) ppm. MS (EI, 70 eV): 185 ([M−CH$_3$]$^+$3), 171 (11), 135 (4), 95 (15), 83 (6), 73 (100), 55 (43), 43 (44), 29 (9).

Odor description: floral, muguet, aldehydic.

Example 5: Preparation of 9-hydroxy-5,9-dimethylundec-4-enal

5a: 5,9-Dimethylundeca-4,8-dienal

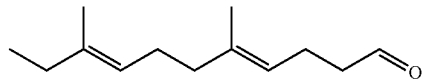

Ethyl Linalool (70.0 g, 416 mmol) and ethyl vinyl ether (90.0 g, 1248 mmol) were placed in an autoclave and phenyl phosphonic acid (1.0 g, 6 mmol) was added. The autoclave was flushed with nitrogen and sealed. The mixture was heated to 220° C. (10 bar) for 1.5 h. The reaction mixture was concentrated in vacuo and the residual crude oil was distilled at 75° C./0.05 bar to afford 5,9-dimethylundeca-4,8-dienal as a colorless liquid (41.1 g, 51%; mixture of E/Z-isomers).

$^1$H-NMR (CDCl$_3$, 400 MHz): 9.76 (m, 1H), 5.10 (m, 2H), 2.45 (m, 2H), 2.32 (m, 2H), 2.16-1.90 (m, 6H), 1.68 (m, 3H), 1.61 (m, 3H), 0.97 (m, 3H). $^{13}$C-NMR (CDCl$_3$, 100 MHz): 202.6, 202.5, 202.4, 137.5, 137.2, 137.0, 136.9, 136.8 (3s), 123.7, 122.8, 122.5, 122.4, 122.0 (2d), 44.2, 44.0, 39.9, 39.6, 32.3, 32.2, 32.0, 26.4, 26.3, 26.2, 26.1, 24, (4t), 23.3, 22.9, 22.8 (q), 20.8, 20.7 (t), 16.0, 15.9, 12.8, 12.7 (2q). MS (EI, 70 eV, main isomer): 194 (M$^+$, 2), 137 (15), 93 (16), 83 (68), 82 (10), 81 (10), 67 (15), 55 (100), 41 (36), 39 (12).

5b: 9-Hydroxy-5,9-dimethylundec-4-enal

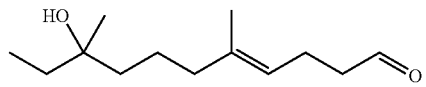

5,9-Dimethylundeca-4,8-dienal (33.0 g, 170 mmol) was placed in a reactor and dichloromethane (500 ml) was added. The mixture was cooled to 0° C. and trifluoroacetic acid (97.0 g, 849 mmol) was added drop wise over 20 minutes while keeping the temperature below 5° C. 10 minutes after the addition GC analysis of the reaction mixture indicated complete conversion. The reaction mixture was poured onto saturated, aqueous sodium carbonate solution (300 ml) and stirred for 10 minutes. Water was added (300 ml) and the mixture was extracted with ether. The organic layers were combined, washed with water and brine, dried over MgSO$_4$ and concentrated in vacuo. The residual oil (44.0 g) was mixed with methanol (500 ml). Sodium methoxide (10.1 g, 187 mmol) was added in portions over the period of 30 minutes at room temperature. The temperature was kept below 25° C. by gently cooling with an ice/water bath. After the addition the mixture was stirred at room temperature for 20 minutes. The reaction mixture was poured onto water (600 ml) and extracted with ether. The organic layers were washed with water and brine, dried over MgSO$_4$ and concentrated in vacuo to afford the crude product (36.0 g). Short path distillation yielded a yellow oil (10.5 g) which was purified by flash chromatography over SiO$_2$ using hexane/EtOAc 7:3 as the eluent. The purified product (7.8 g) was dissolved in acetone (150 ml) and treated with HCl 2M (5 ml). The solution was heated to 50° C. for 10 minutes to hydrolyse the dimethyl acetal present in the product. Water (300 ml) was added and the mixture extracted with ether. The layers were separated; the organic layer was washed with water and brine, dried over MgSO$_4$ and concentrated in vacuo. The residue was distilled bulb to bulb at 140° C., 0.05 mbar to afford the product as a colorless oil (3.5 g, 10%, E/Z isomers, ratio ca. 2:3).

$^1$H-NMR (CDCl$_3$, 400 MHz): 9.74 (s, 1H), 5.09 (t, J=7.09 Hz, 1H), 2.44 (m, 2H), 2.31 (m, 2H), 2.02 (m, 1H), 1.95 (m, 1H), 1.66 (s, 1.2H), 1.60 (s, 1.8H), 1.51-1.31 (m, 7H), 1.12 (s, 3H), 0.91-0.84 (m, 3H). $^{13}$C-NMR (CDCl$_3$, 100 MHz): 202.2 (d), 137.0, 136.7 (s), 122.8, 122.1 (d), 72.7 (s), 44.1, 43.9, 41.0, 40.8, 40.0, 34.3, 34.2, 32.0 (4t), 26.35, 23.3 (q), 22.111, 22.0, 20.8, 20.6 (2t), 15.9, 8.2 (2q). MS (EI, 70 eV, main isomer): 194 (M$^+$-H$_2$O, 1), 124 (70), 107 (42), 96 (59), 95 (39), 81 (100), 73 (78), 68 (37), 55 (77), 43 (58).

Odor description: floral, watery, aldehydic

The invention claimed is:

1. A compound according to formula I

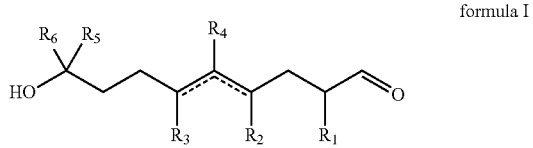

formula I wherein:

⌒ represents a double bond either at $C_4$ or at $C_5$:

$R_1$, $R_2$, $R_3$, $R_4$ are independently selected from H or Me; and, $R_5$, $R_6$ are independently selected from Me or Et, and wherein the compound is not 9-hydroxy-5,9-dimethyldec-4-enal.

2. A pro-perfume, adapted to provide the compound represented by the formula I

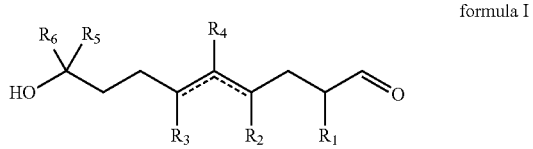

formula I wherein;

⌒ represents a double bond either at $C_4$ or at $C_5$, or represents single bonds;

$R_1$, $R_2$, $R_3$, $R_4$ are independently selected from H or Me, and $R_5$, $R_6$ are independently selected from Me or Et, and wherein the compound is not 9-hydroxy-5,9-dimethyldec-4-enal, 9-hydroxy-5,9-dimethyldecanal, or 9-hydroxy-9-methyldecanal.

3. A compound according to formula I which is a perfume ingredient.

4. The perfume ingredient of claim 3 which has muguet odour characteristics.

5. A perfume composition comprising a compound according to the formula I.

6. A perfume composition according to claim 5 comprising one or more additional fragrance ingredients.

7. A perfume composition according to claim 5 that is free of 4(4-hydroxy-4-methylpentyl) 3-cyclohexane carboxaldehyde.

8. A muguet perfume composition according to claim 6.

9. A personal care product or household care product or fine fragrance comprising at least a compound according to claim 1.

10. A method of imparting muguet odour characteristics to a personal care product or household care product or fine fragrance, said method comprising the step of: including therein a compound according to claim 1.

11. A perfume composition according to claim 5 which additionally comprises an anti-oxidant.

12. The pro-perfume of claim 2 which is an aminal and/or enamine of the compound of formula I.

13. The pro-perfume of claim 2 which is a perfume ingredient.

14. The pro-perfume of claim 2 which had muguet odour characteristics.

15. A perfume composition comprising a pro-perfume according to claim 2.

16. A perfume composition according to claim 6, where the additional fragrance ingredient is (E/Z)-9-hydroxy-5,9-dimethyldec-4-enal.

17. A personal care product or household care product or fine fragrance comprising at least a pro-perfume according to claim 2.

18. A personal care product or household care product or fine fragrance comprising a perfume composition according to claim 5.

19. A personal care product or household care product or fine fragrance comprising a perfume composition according to claim 6.

20. A personal care product or household care product or fine fragrance comprising a perfume composition according to claim 7.

* * * * *